US012582787B2

(12) United States Patent     (10) Patent No.:   US 12,582,787 B2

Inoue et al.     (45) Date of Patent:    Mar. 24, 2026

(54) MASK OUTER FRAME UNIT, MASK UNIT, BAND-INCLUDING MASK UNIT AND MASK OUTER FRAME

(71) Applicant: NIHON KOHDEN CORPORATION, Tokyo (JP)

(72) Inventors: Masayuki Inoue, Tokorozawa (JP); Yuya Baba, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 453 days.

(21) Appl. No.: 17/104,977

(22) Filed: Nov. 25, 2020

(65)       Prior Publication Data

US 2021/0170130 A1     Jun. 10, 2021

(30)       Foreign Application Priority Data

Dec. 6, 2019    (JP) ................................. 2019-221084

(51) Int. Cl.
*A61M 16/06*       (2006.01)

(52) U.S. Cl.
CPC .... *A61M 16/0633* (2014.02); *A61M 16/0622* (2014.02); *A61M 16/0683* (2013.01)

(58) Field of Classification Search
CPC ........... A61M 16/0622; A61M 16/0633–0655; A61M 16/0683
See application file for complete search history.

(56)       References Cited

U.S. PATENT DOCUMENTS

| | | | |
|---|---|---|---|
| 6,119,693 A | * | 9/2000 | Kwok ............... A61M 16/0633 |
| | | | 128/207.18 |
| 6,520,182 B1 | * | 2/2003 | Gunaratnam ....... A61M 16/065 |
| | | | 128/207.11 |
| D586,258 S | | 2/2009 | Guney et al. |
| 10,076,627 B2 | | 9/2018 | Hitchcock et al. |
| 2003/0034034 A1 | * | 2/2003 | Kwok ............... A61M 16/0666 |
| | | | 128/207.13 |
| 2003/0075180 A1 | | 4/2003 | Raje et al. |
| 2003/0075182 A1 | * | 4/2003 | Heidmann ............ A61M 16/06 |
| | | | 128/207.11 |
| 2004/0112384 A1 | | 6/2004 | Lithgow et al. |
| 2004/0112385 A1 | | 6/2004 | Drew et al. |

(Continued)

FOREIGN PATENT DOCUMENTS

| | | |
|---|---|---|
| JP | 2005-537904 A | 12/2005 |
| JP | 2008-526395 A | 7/2008 |
| WO | WO-2005123166 A1 * 12/2005 | ........ A61M 16/0003 |

OTHER PUBLICATIONS

Japanese Office Action issued Jun. 27, 2023 corresponding to Japanese Office Action 2019-221084.

*Primary Examiner* — Valerie L Woodward

(74) *Attorney, Agent, or Firm* — McDonald Hopkins LLC

(57)       ABSTRACT

A mask outer frame unit includes a mask outer frame which can be mounted on a mask attached to a face of a patient, and a pad that can abut against the face of the patient. The mask outer frame includes a forehead contact portion which is disposed so as to make the pad abut against a forehead of the patient. An adjustment portion to which the pad can be attached removably, and which can adjust at least one of an angle of the pad with respect to the forehead contact portion and a position of the pad with respect to the forehead contact portion is provided in the forehead contact portion.

9 Claims, 6 Drawing Sheets

(56)     References Cited

U.S. PATENT DOCUMENTS

| | | | |
|---|---|---|---|
| 2004/0112387 A1* | 6/2004 | Lang | A61M 16/0644 128/206.24 |
| 2004/0118406 A1 | 6/2004 | Lithgow et al. | |
| 2005/0005940 A1* | 1/2005 | Gunaratnam | A61M 16/0622 128/207.11 |
| 2005/0081858 A1 | 4/2005 | Raje et al. | |
| 2006/0102185 A1 | 5/2006 | Drew et al. | |
| 2007/0157353 A1 | 7/2007 | Guney et al. | |
| 2007/0157934 A1 | 7/2007 | Lang et al. | |
| 2008/0099014 A1 | 5/2008 | Drew et al. | |
| 2008/0178885 A1 | 7/2008 | Raje et al. | |
| 2009/0178679 A1 | 7/2009 | Lithgow et al. | |
| 2010/0163049 A1* | 7/2010 | Osier | A61M 16/0611 29/428 |
| 2010/0236559 A1 | 9/2010 | Lithgow et al. | |
| 2010/0275923 A1 | 11/2010 | Guney et al. | |
| 2011/0056498 A1 | 3/2011 | Lang et al. | |
| 2011/0220114 A1 | 9/2011 | Lithgow et al. | |
| 2012/0174928 A1 | 7/2012 | Raje et al. | |
| 2012/0216819 A1 | 8/2012 | Raje et al. | |
| 2014/0202464 A1 | 7/2014 | Lithgow et al. | |
| 2014/0230822 A1* | 8/2014 | Kuo | A61M 16/0683 128/206.21 |
| 2014/0238404 A1 | 8/2014 | Guney et al. | |
| 2014/0261412 A1 | 9/2014 | Guney et al. | |
| 2014/0373848 A1 | 12/2014 | Drew et al. | |
| 2015/0190601 A1 | 7/2015 | Lang et al. | |
| 2016/0339195 A1 | 11/2016 | Raje et al. | |
| 2017/0296768 A1 | 10/2017 | Guney | |
| 2018/0133426 A1* | 5/2018 | Hallett | A61M 16/06 |

* cited by examiner

1

MASK OUTER FRAME UNIT, MASK UNIT, BAND-INCLUDING MASK UNIT AND MASK OUTER FRAME

CROSS-REFERENCE TO RELATED APPLICATIONS

The present application claims priority from Japanese Patent Application No. 2019-221084 filed on Dec. 6, 2019, the entire content of which is incorporated herein by reference.

TECHNICAL FIELD

The presently disclosed subject matter relates to a mask outer frame unit, a mask unit, a band-including mask unit, and a mask outer frame.

BACKGROUND ART

When artificial respiration is performed by non-invasive positive pressure ventilation, continuous positive airway pressure, or the like, a mask is attached to the face of a patient. On this occasion, it is desirable that the mask is firmly fixed to the face of the patient. However, since the size of the face of one patient varies from the size of the face of another patient, it is necessary to, for example, adjust the position of a portion of the mask in contact with the forehead of the patient in order to attach the mask to a suitable position. Patent document JP-T-2008-526395 discloses a mask assembly provided with a head frontal region support body having a slide bar which can slide.

When the artificial respiration is performed by use of the non-invasive positive pressure ventilation, the continuous positive airway pressure, or the like, strong compression pressure is applied to a portion of the patient's face in contact with the mask. In addition, the mask can be attached to the patient for a relatively long time.

Accordingly, there is a fear that a feeling of discomfort is caused to the patient due to the strong compression pressure applied to the same place of the patient wearing the mask for a long time. In this respect, the mask assembly according to Patent document JP-T-2008-526395 still has room for improvement.

SUMMARY

An object of the presently disclosed subject matter is to provide a mask outer frame unit, a mask unit, a band-including mask unit, and a mask outer frame each of which can lighten a feeling of discomfort caused to a patient with a simple configuration.

The mask outer frame unit according to an aspect in order to achieve the aforementioned object is a mask outer frame unit that can include:

a mask outer frame that can be mounted on a mask attached to a face of a patient; and a pad that can abut against the face of the patient; wherein:

the mask outer frame has a forehead contact portion that is disposed so as to make the pad abut against a forehead of the patient; and the forehead contact portion is provided with an adjustment portion to which the pad can be attached removably and that can adjust at least one of an angle of the pad with respect to the forehead contact portion and a position of the pad with respect to the forehead contact portion.

2

The mask unit according to an aspect in order to achieve the aforementioned object can include:

the mask outer frame unit; and a mask that can be attached to the face of the patient.

The band-including mask unit according to an aspect in order to achieve the aforementioned object can include:

the mask unit; and bands that can be placed into the mask unit and that can be attached to the patient.

The mask outer frame according to an aspect in order to achieve the aforementioned object is a mask outer frame that can be mounted on a mask attached to a face of a patient, wherein:

the mask outer frame includes a forehead contact portion that is disposed so as to make a pad abuttable against the face of the patient abut against a forehead of the patient;

an adjustment portion for removably attaching the pad thereto is provided in the forehead contact portion; and the adjustment portion can adjust at least one of an angle of the pad with respect to the forehead contact portion and a position of the pad with respect to the forehead contact portion.

According to the aforementioned configuration, the adjustment portion to which the pad can be removably attached and that can adjust at least one of an angle of the pad with respect to the forehead contact portion and a position of the pad with respect to the forehead contact portion is provided in the forehead contact portion. Accordingly, it is possible to easily change the angle of the pad with respect to the forehead contact portion or the position of the pad with respect to the forehead contact portion without changing the position of the mask or the outer frame.

Thus, according to the aforementioned configuration, it is possible to lighten a feeling of discomfort caused to the patient with a simple configuration.

DESCRIPTION OF EMBODIMENT

An embodiment will be described below in detail by way of example with reference to the accompanying drawings. Incidentally, "up", "down", "left", "right", "front" and "rear" used in the specification and the drawings of the presently disclosed subject matter denote directions displayed for convenience of explanation, and are not intended to be limited to the illustrated directions.

Figure 1:
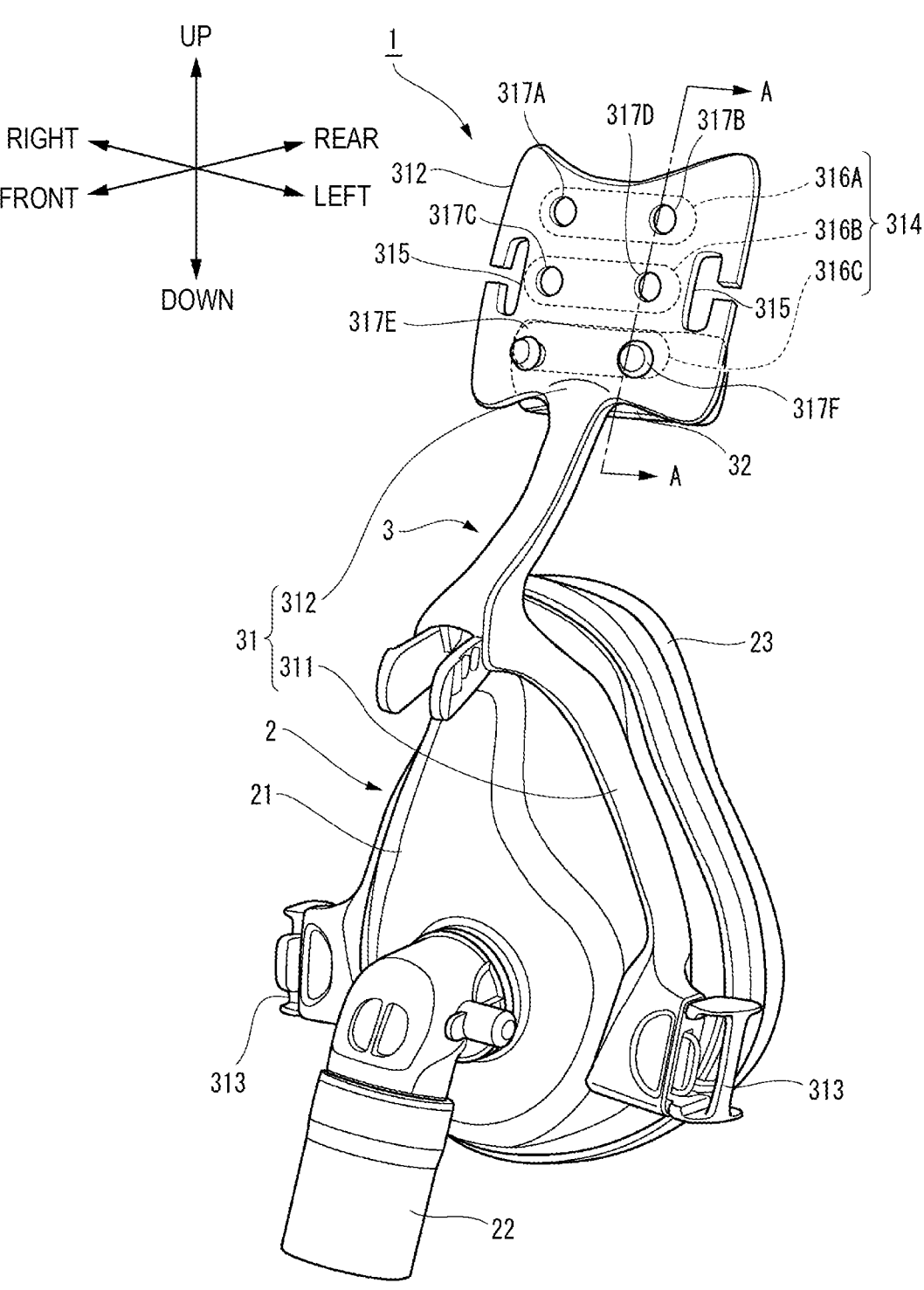
FIG. 1 is a view illustrating external appearance of a mask unit according to an embodiment.

FIG. 1 is a perspective view of a mask unit 1 according to an embodiment. The mask unit 1 can be used when, for example, non-invasive positive pressure ventilation (NPPV) or continuous positive airway pressure (CPAP) is used in treatment of chronic respiratory failure or artificial respiration.

As illustrated in FIG. 1, the mask unit 1 may include a mask 2, and a mask outer frame unit 3 (hereinafter also referred to as outer frame unit 3 simply).

The mask 2 may include a mask body portion 21, a hose connection portion 22, and a cushion member 23.

The mask body portion 21 is formed into a shape which covers the nose and the mouth of a patient while forming a space for the patient to breathe through his/her nose and mouth. The mask body portion 21 has at least a portion transparent or semitransparent so that the nose and the mouth of the patient can be visually recognized through the transparent or semitransparent portion. The mask body portion 21 is preferably formed out of a hard resin material. Such a resin material is, for example, polycarbonate.

The hose connection portion 22 is formed into a tabular shape. The hose connection portion 22 is provided in a lower portion of the mask body portion 21 so as to make the space of the mask body portion 21 communication with an external space. The hose connection portion 22 is formed out of a hard resin material such as polycarbonate.

The cushion member 23 is provided along, of the mask body portion 21, a circumferential edge portion making contact with the face of the patient. The cushion member 23 is formed out of a soft resin material so that the cushion member 23 can be flexibly deformed to be kept airtight against the face of the patient.

The outer frame unit 3 may include a mask outer frame 31 (hereinafter also referred to outer frame 31 simply), and a pad 32.

The outer frame 31 may include a mounting portion 311 and a forehead contact portion 312. The outer frame 31 is formed out of a hard resin material such as polycarbonate.

The mounting portion 311 is formed into an inverted Y-shape in front view to extend upward from an upper portion of the mask body portion 21 and extend from the upper portion of the mask body portion 21 toward the left and right of a lower portion of the mask portion 21. The mounting portion 311 is mounted on the upper portion of the mask body portion 21 and the left and right places of the lower portion of the mask body portion 21. The mounting portion 311 may include first band attachment portions 313 at its lower left end portion and its lower right end portion respectively. Each of the first band attachment portions 313 has an I-shaped frame structure through which a band 41 (see FIG. 4) can be inserted in a front/rear direction to be then folded back to the left or right.

As illustrated in FIG. 1, the forehead contact portion 312 is disposed so as to make the pad 32 abut against the forehead of the patient. The forehead contact portion 312 is a plate-like portion formed continuously to an upper end of the mounting portion 311. In the present example, the external shape of the forehead contact portion 312 in front view is an approximately quadrilateral shape whose corner portions have been chamfered. Incidentally, the forehead contact portion 312 may be configured to be curved in accordance with the shape of the forehead.

Second band attachment portions 315 are provided respectively at the centers of left and right end portions of the forehead contact portion 312. Each of the second band attachment portions 315 has a hook-shaped lock structure through which a band 41 (see FIG. 4) can be inserted in the front/rear direction to be then folded back to the left or right.

An adjustment portion 314 to which the pad 32 can be removably attached and which can adjust at least one of an angle (posture) and a position of the pad 32 with respect to the forehead contact portion 312 is provided in the forehead contact portion 312.

The adjustment portion 314 in the present example may include a first attachment portion 316A, a second attachment portion 316B and a third attachment portion 316C which are attachment portions for attaching the pad 32 thereto.

Each of the first attachment portion 316A, the second attachment portion 316B and the third attachment portion 316C may include a pair of left and right circular through holes (an example of attachment regions or engagement recesses). The first attachment portion 316A, the second attachment portion 316B and the third attachment portion 316C are disposed side by side in an up/down direction in the forehead contact portion 312. The first attachment portion 316A provided in an upper part may include a first right through hole 317A and a first left through hole 317B. The second attachment portion 316B provided in an intermediate part may include a second right through hole 317C and a second left through hole 317D. The third attachment portion 136C provided in a lower part may include a third right through hole 317E and a third left through hole 317F. The corresponding ones of the through holes 317A to 317F provided in each of the mounting portions 316A to 316C can be engaged with engagement protrusions 322 of the pad 32 which will be described later.

Figure 2:
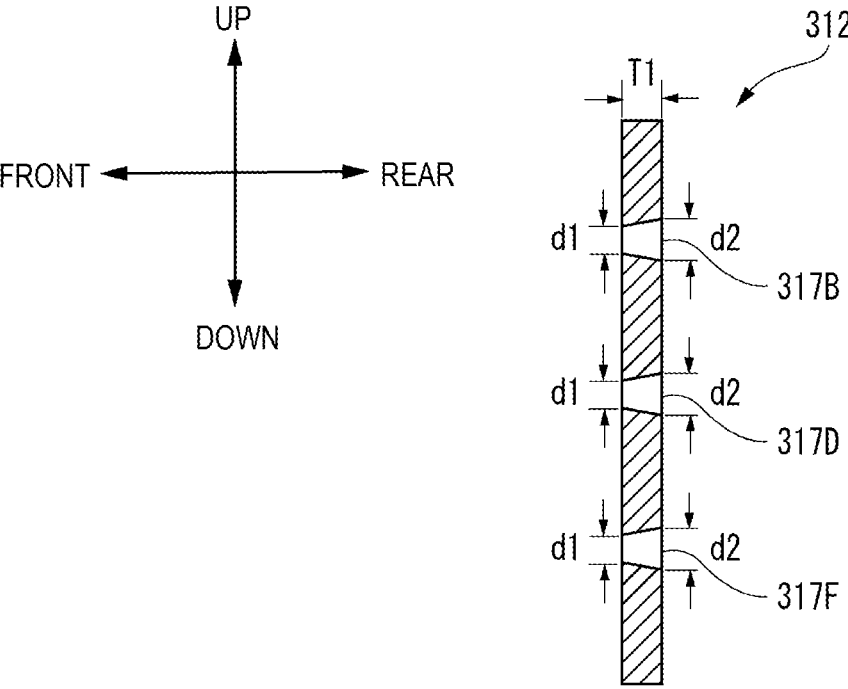
FIG. 2 is a view of a section taken along a line A-A of FIG. 1.

FIG. 2 is a view of a section taken along a line A-A in FIG. 1 to illustrate only the forehead contact portion 312.

As illustrated in FIG. 2, each of the first left through hole 317B, the second left through hole 317D and the third left through hole 317F is formed so as to make its diameter larger toward the rear. The rear of the forehead contact portion 312 is a side on which a body portion of the pad 32 attached to one of the first attachment portion 316A, the second attachment portion 316B and the third attachment portion 316C is disposed. In each of the first left through hole 317B, the second left through hole 317D and the third left through hole 317F, a diameter d2 of a rear end is larger than a diameter d1 of a front end. The first right through hole 317A, the second right through hole 317C and the third right through hole 317E also have a sectional structure similar to or the same as that of the first left through hole 317B, the second left through hole 317D and the third left through hole 317F.

Figures 3A, 3B:
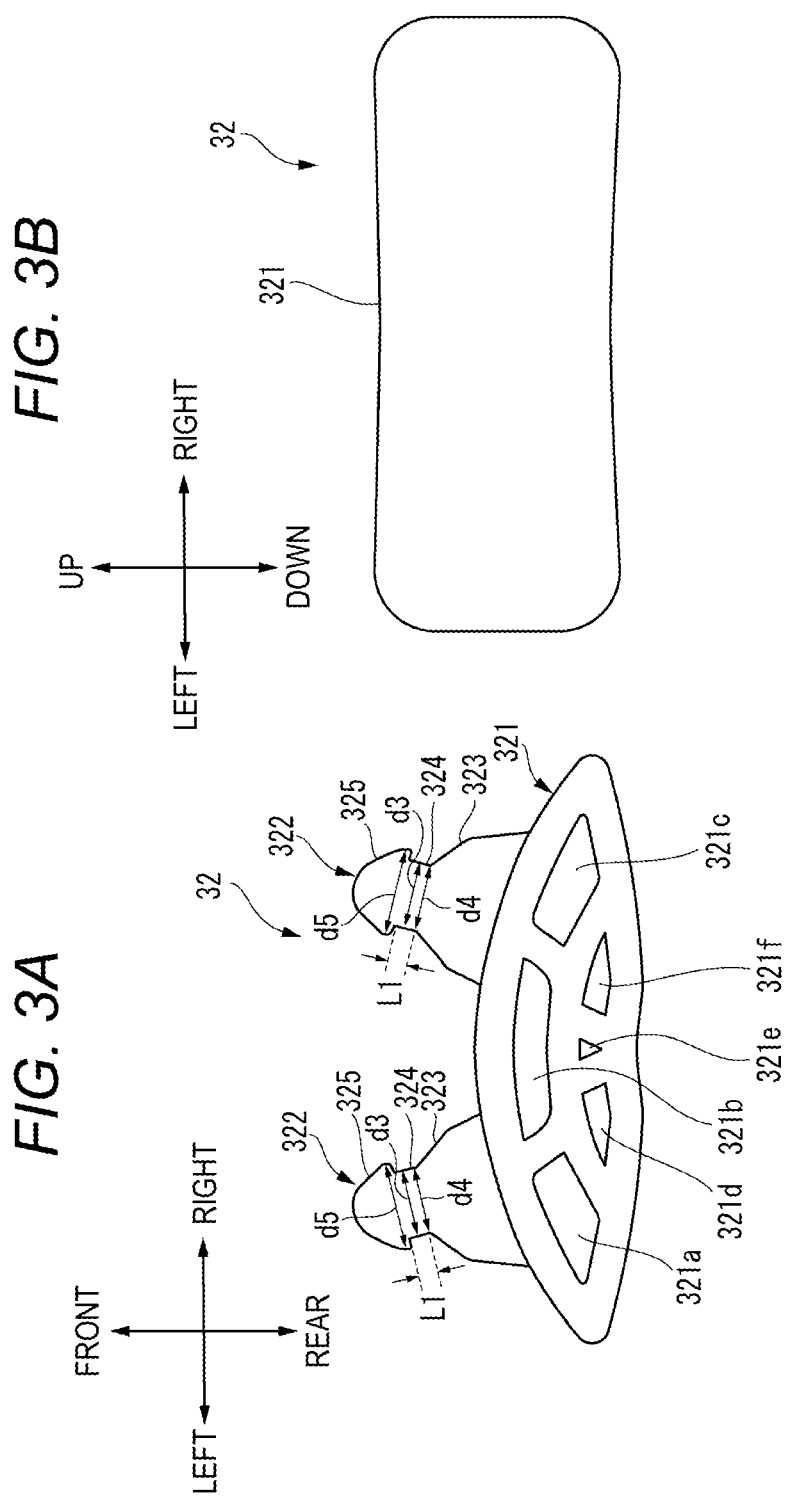
FIGS. 3A and 3B are a bottom view of a pad to be attached to a forehead contact portion, and a view illustrating a rear face of the pad to be attached to the forehead contact portion.

Next, the pad 32 will be described with reference to FIGS. 3A and 3B. FIG. 3A is a bottom view of the pad 32 to be attached to the forehead contact portion 312. FIG. 3B is a view illustrating a rear face of the pad 32 to be attached to the forehead contact portion 312. The pad 32 is a buffer material disposed between the forehead contact portion 312 and the forehead of the patient. The pad 32 is, for example, made of a soft resin and can be elastically deformed. As illustrated in FIG. 3A, the pad 32 may include a pad body portion 321 and engagement protrusions 322. The pad body portion 321 may include a plurality of cavities 321a to 321f internally. Due to the cavities 321a to 321f provided in the pad body portion 321, the pad body portion 321 can expand and contract in the front/rear direction easily. That is, the pad body portion 321 has a cushion function. Incidentally, the pad body portion 321 according to the present embodiment has six cavities 321a to 321f. However, the number of the cavities is not limited thereto as long as the pad body portion 321 can exert the cushion function. In addition, the pad body portion 321 does not have to be configured to have the cavities.

As illustrated in FIG. 3B, the rear face of the pad body portion 321 has an approximately rectangular shape. However, the shape of the rear face of the pad body portion 321 may be any other shape such as a square shape or a circular shape.

Next, the engagement protrusions 322 will be described with reference to FIG. 3A. The engagement protrusions 322 are regions serving for engaging the pad 32 with one of the attachment portions 316A to 316C. The engagement protrusions 322 are provided on the left and the right to be paired. Each of the engagement protrusions 322 may include a pedestal portion 323, a cylindrical column portion 324, and a truncated cone portion 325. The pedestal portion 323 is a mountain type. The pedestal portion 323 is formed continuously to the pad body portion 321.

The cylindrical column portion 324 is disposed between the pedestal portion 323 and the truncated cone portion 325. The cylindrical column portion 324 is formed continuously to the pedestal portion 323 and the truncated cone portion 325. A diameter d3 of the cylindrical column portion 324 is substantially equal to a diameter d4 of a front end of the pedestal portion 323. The diameter d3 of the cylindrical column portion 324 is smaller than a diameter d5 of a rear end of the truncated cone portion 325.

The diameter d3 of the cylindrical column portion 324 is smaller than the diameter d2 on the rear side of each through hole 317A to 317F (see FIG. 2). The diameter d3 of the cylindrical column portion 324 is substantially equal to the diameter d1 on the front side of the through hole 317A to 317F (see FIG. 2). The diameter d5 of the rear end of the truncated cone portion 325 is larger than the aforementioned diameter d1. In addition, a length LI of the cylindrical column portion 324 in the front/rear direction is substantially equal to a thickness TI of the forehead contact portion 312 in the front/rear direction (see FIG. 2).

To attach the pad 32 to one of the first attachment portion 316A, the second attachment portion 316B and the third attachment portion 316C, a user such as a medical worker brings the truncated cone portions 325 of the engagement protrusions 322 into contact with ones of the through holes 317A to 371F and presses the truncated cone portions 325 into the ones of the through holes 317A to 371F so as to elastically deform the truncated cone portions 325. As a result, each of the diameters of the truncated cone portions 325 becomes smaller than the diameter d1 on the front side of each through hole 317A to 317F. In the state where the truncated cone portions 325 have been elastically deformed, the user such as the medical worker presses the truncated cone portions 325 forward. Thus, the truncated cone portions 325 are inserted into, of the through holes 317A to 317F, the through holes into which the user desires to insert the pad 32. That is, the engagement protrusions 322 are inserted into, of the through holes 317A to 317F, the through holes into which the user desires to insert the pad 32. When the truncated cone portions 325 are inserted into the through holes of the through holes 317A to 317F, and moved forward from the through holes into which the truncated cone portions 325 have been inserted, the truncated cone portions 325 are restored to their original states. Since the diameter d5 of each of the rear ends of the truncated cone portions 325 is larger than the diameter d1 of each of the through holes 317A to 317F, the truncated cone portions 325 are engaged with the through holes of the through holes 317A to 317F. As a result, the truncated cone portions 325 are restricted from moving rearward so that the pad 32 can be restrained from coming off rearward from the forehead contact portion 312.

Figure 4:
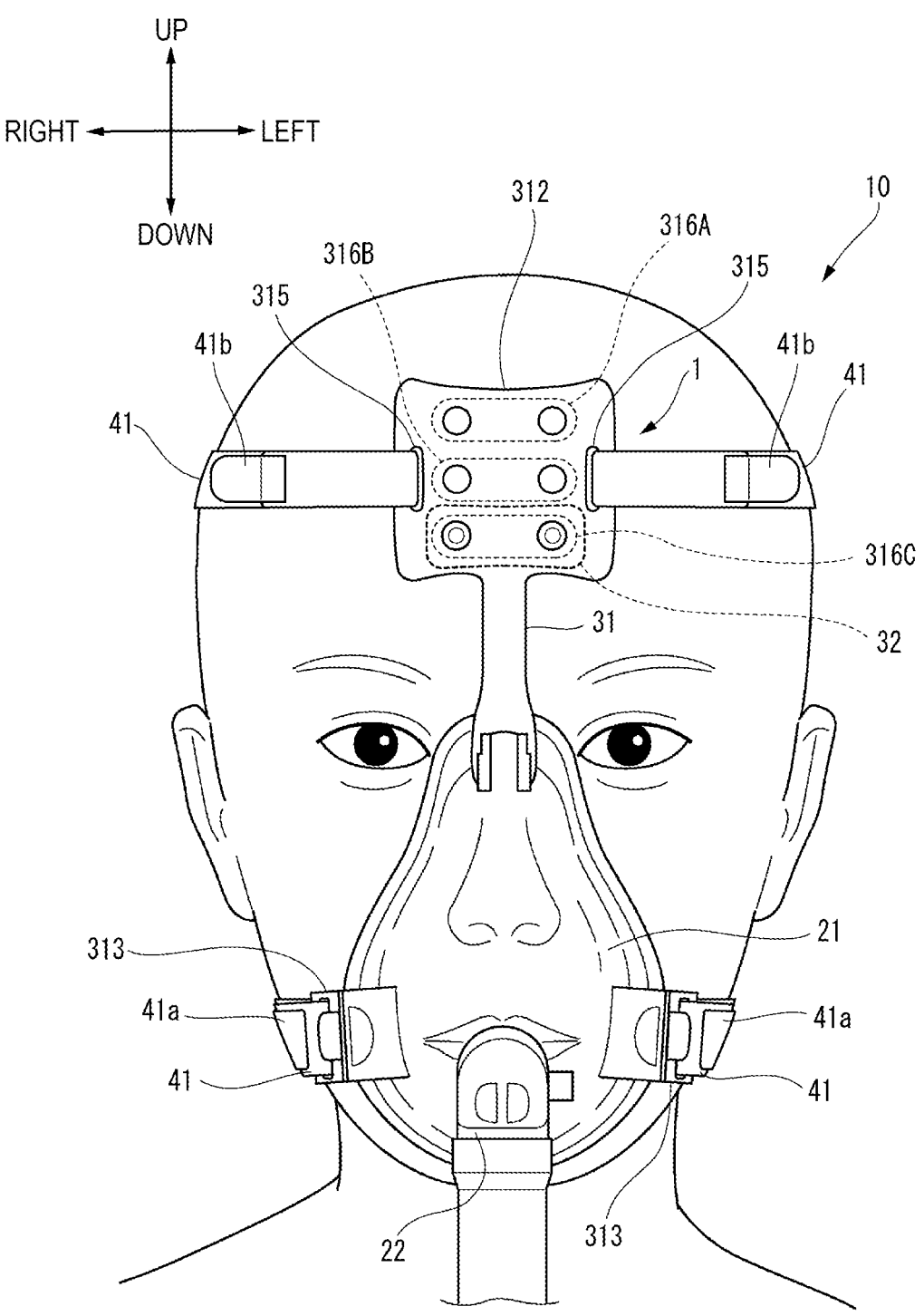
FIG. 4 is a view illustrating a use example of a band-including mask unit.

Next, a band-including mask unit 10 will be described with reference to FIG. 4. FIG. 4 is a view illustrating a use example of the band-including mask unit 10. The band-including mask unit 10 may include the mask unit 1 and bands 41. In the band-including mask unit 10, the bands 41 are inserted through the first band attachment portions 313 and the second band attachment portions 315 respectively. Of each of the bands 41, a portion passing through the cheek of a patient is inserted through one of the first band attachment portions 313 from the rear toward the front to be then folded back to the left or the right. An end portion 41a of the band 41 is pasted to a portion of the band 41 positioned near the cheek of the patient, for example, by use of a hook-and-loop fastener. Of each of the bands 41, a portion passing through the head of the patient is inserted through one of the first band attachment portions 315 from the rear toward the front to be then folded back to the left or the right. An end portion 41b of the band 41 is pasted to a portion of the band 41 positioned near the head of the patient, for example, by use of a hook-and-loop fastener. The bands 41 can fix the band-including mask unit 10 to the cheek and the head of the patient. The bands 41 are formed out of a material having elasticity. For example, silicone rubber or the like can be used as such a material.

Here, a use example of the band-including mask unit 10 will be described. First, a user such as a medical worker attaches the pad 32 to one of the first attachment portion 316A, the second attachment portion 316B and the third attachment portion 316C. In the example illustrated in FIG. 4, the pad 32 is attached to the third attachment portion 316C.

Next, the user attaches the bands 41 to the patient so as to surround the cheek and the head of the patient. Thus, in a state where the pad 32 has abutted against the forehead of the patient, the band-including mask unit 10 is fixed to the patient. When the band-including mask unit 10 is attached to the patient, for example, artificial respiration is started.

When the artificial respiration is performed by non-invasive positive pressure ventilation, continuous positive airway pressure, or the like, the mask is attached to the face of the patient. On this occasion, the mask is firmly fixed to the face of the patient. However, in order to reduce leak between the face of the patient and the mask, strong compression pressure is applied to the face of the patient. The mask is attached to the patient for a relatively long time. Accordingly, when the artificial respiration is performed by use of a background-art mask, there is a fear that a feeling of discomfort is caused to the patient due to the strong compression pressure applied to the same place for a long time.

In order to solve such a problem, the mask unit 1 is used as follows. When a predetermined time elapses after the artificial respiration is started, the user first removes the bands 41 fixed to the head of the patient from the head of the patient, and then moves the forehead contact portion 312 forward to cancel the abutment state between the pad 32 and the forehead of the patient in order to change the attachment position of the pad 32. For example, to change the attachment position of the pad 32 from the third attachment portion 316C to the second attachment portion 316B, the user first applies rearward force to the pad 32. As a result, the truncated cone portions 325 are elastically deformed by the through holes 317E and 317F respectively so that the diameters of the truncated cone portions 325 can be smaller. The user pulls the pad 32 rearward while elastically deforming the truncated cone portions 325. Accordingly, the user removes the engagement protrusions 322 from the third right through hole 317E and the third left through hole 317F. Thus, the pad 32 is detached from the third attachment portion 316C. The user then inserts the engagement protrusions 322 into the second right through hole 317C and the second left through hole 317D while elastically deforming the truncated cone portions 325 of the engagement protrusions 322. As a result, the user attaches the pad 32 to the second attachment portion 316B.

According to the aforementioned configuration, it is possible to easily change the position where the compression pressure is applied to the patient by only changing not the position of the mask 2 or the outer frame 31 but the attachment position of the pad 32 (the attachment position of the pad 32 to the forehead contact portion 312). Accordingly, a feeling of discomfort caused to the patient can be lightened with a simple configuration.

In addition, according to the aforementioned configuration, the adjustment portion 314 includes the first attachment portion 316A, the second attachment portion 316B and the third attachment portion 316C which are the attachment portions for attaching the pad 32 thereto. Accordingly, the position where the pad 32 is in contact with the forehead of the patient can be changed while the position of the forehead contact portion 312 having the adjustment portion 314 is maintained as it is.

In addition, according to the aforementioned configuration, each of the first attachment portion 316A, the second attachment portion 316B and the third attachment portion 316C includes a pair of left and right circular through holes. The first attachment portion 316A, the second attachment portion 316B and the third attachment portion 316C are disposed side by side in the up/down direction in the forehead contact portion 312. Accordingly, the position where the pad 32 is in contact with the forehead of the patient can be changed in the up/down direction while the position of the forehead contact portion 312 having the adjustment portion 314 is maintained as it is.

In addition, according to the aforementioned configuration, the engagement protrusions 322 are provided in the pad 32. The through holes functioning as engagement recesses are provided in each of the attachment portions 316A to 316C. The pad 32 is softer than the attachment portion 316A to 316C. Accordingly, the pad 32 can secure an elastic deformation amount for sufficiently exerting the cushion function required of the pad 32 without excessively increasing the thickness of the pad 32, in comparison with a case where the engagement protrusions 322 are provided in each of the attachment portions 316A to 316C, and the through holes functioning as engagement recesses are provided in the pad 32.

In addition, according to the aforementioned configuration, each of the first attachment portion 316A, the second attachment portion 316B and the third attachment portion 316C includes a pair of left and right circular through holes. Accordingly, the engagement protrusions 322 of the pad 32 are easily engaged with any one of the attachment portions 316A to 316C.

In addition, according to the aforementioned configuration, each of the through holes 317A to 317F in the adjustment portion 314 is formed so that the diameter of the through hole 317A to 317F is larger toward the rear of the forehead contact portion 312, i.e. toward the side on which the body portion of the pad 32 attached to one of the first attachment portion 316A, the second attachment portion 316B and the third attachment portion 316C is disposed.

Accordingly, the pad 32 can be prevented from easily coming off from the corresponding ones of the through holes 317A to 317F.

Modifications each having a different configuration of a forehead contact portion from the configuration of the forehead contact portion 312 in the aforementioned embodiment will be described below.

First Modification

Figure 5:
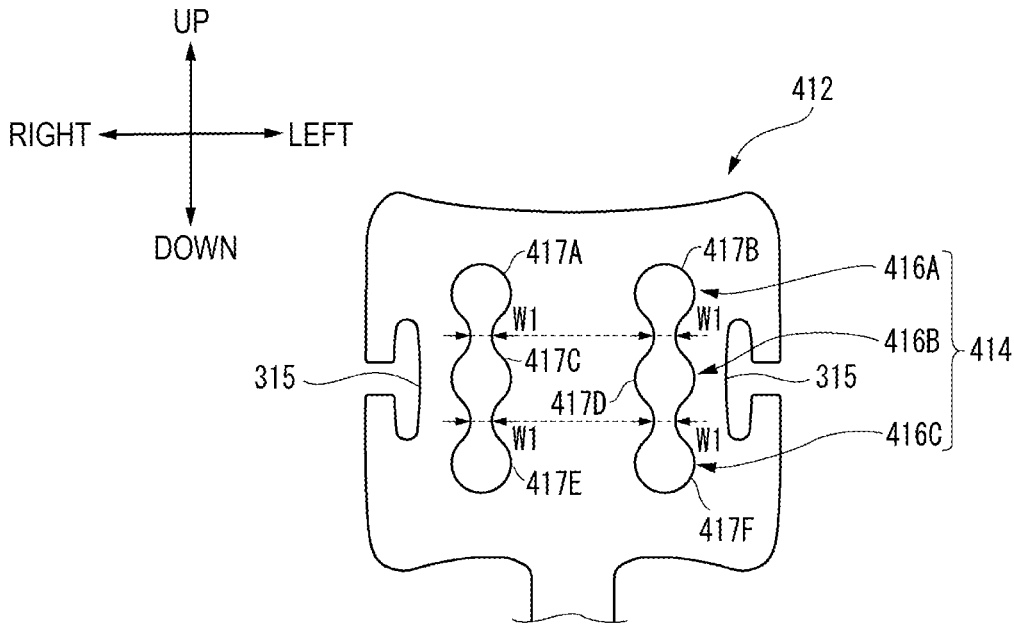
FIG. 5 is a view illustrating a forehead contact portion according to a first modification.

FIG. 5 is a view illustrating a forehead contact portion 412 according to a first modification. The forehead contact portion 412 is different from the forehead contact portion 312 at a point that an adjustment portion 414 different in configuration from the adjustment portion 314 is provided.

The adjustment portion 414 may include a first attachment portion 416A, a second attachment portion 416B, and a third attachment portion 416C.

The adjustment portion 414 is different in configuration from the adjustment portion 314 at a point that the first attachment portion 416A and the second attachment portion 416B are formed continuously to each other, and the second attachment portion 416B and the third attachment portion 416C are formed continuously to each other.

Each of a first right through hole 417A and a first left through hole 417B of the first attachment portion 416A may include a portion which extends downward so as to be smaller in width in the left/right direction to be connected to the second attachment portion 416B. Each of a second right through hole 417C and a second left through hole 417D of the second attachment portion 416B may include a portion which extends upward so as to be smaller in width in the left/right direction to be connected to the first attachment portion 416A. Each of the second right through hole 417C and the second left through hole 417D of the second attachment portion 416B may include a portion which extends downward so as to be smaller in width in the left/right direction to be connected to the third attachment portion 416C. Each of a third right through hole 417E and a third left through hole 417F of the third attachment portion 416C may include a portion which extends upward so as to be smaller in width in the left/right direction to be connected to the second attachment portion 416B.

Widths W1 of the portions where the first attachment portion 416A and the second attachment portion 416B are connected to each other, and the portions where the second attachment portion 416B and the third attachment portion 416C are connected to each other are smaller than the diameter d3 of the cylindrical column portion 324 of the pad 32.

To change the attachment position of the pad 32 on the forehead contact portion 412 according to the first modification, a user can move the pad 32 among the attachment portions 416A to 416C by use of the portions where the first attachment portion 416A and the second attachment portion 416B are connected to each other or the portions where the second attachment portion 416B and the third attachment portion 416C are connected to each other. That is, the user can adjust the position of the pad 32 with respect to the forehead contact portion 412 by only sliding the pad 32 among the attachment portions 416A to 416C without detaching the pad 32 from the forehead contact portion 412.

(Second Modification)

Figure 6:
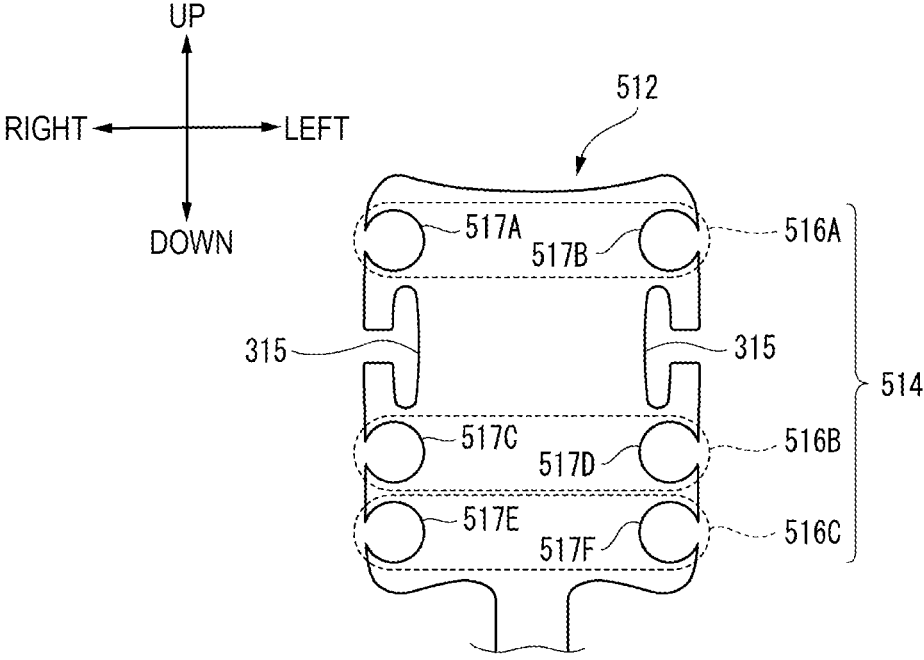
FIG. 6 is a view illustrating a forehead contact portion according to a second modification.

FIG. 6 is a view illustrating a forehead contact portion 512 according to a second modification. The forehead contact portion 512 is different from the forehead contact portion 312 at a point that an adjustment portion 514 different in configuration from the adjustment portion 314 is provided. The adjustment portion 514 may include a first attachment portion 516A, a second attachment portion 516B, and a third attachment portion 516C.

Each of through holes 517A to 517F is disposed to partially overlap with a left or right end portion of the forehead contact portion 512. Accordingly, the through hole 517A to 517F includes an opening portion in the left or the right. A length of the opening portion in an up/down direction is smaller than the diameter d3 of the cylindrical column portion 324 of the pad 32. In addition, second band attachment portions 315 are provided between the first attachment portion 516A and the second attachment portion 516B. However, the second band attachment portions 315 may be provided at different places.

To change the attachment position of the pad 32 on the forehead contact portion 512 according to the second modification, the user first moves the engagement protrusions 322 of the pad 32 so as to remove the engagement protrusions 322 leftward or rightward from ones of the opening portions of the through holes 517A to 517F, i.e. so as to widen the left and right engagement protrusions 322 of the pad 32 in the left/right direction, while elastically deforming the cylindrical column portions 324 of the pad 32. Thus, the pad 32 is detached from one of the attachment portions 516A to 516C to which the pad 32 was attached. The user then moves the engagement protrusions 322 of the pad 32 so as to press the engagement protrusions 322 leftward or rightward into the opening portions of another of the attachment portions 516A to 516C to which the user desires to attach the pad 32 while elastically deforming the cylindrical column portion 324 of the pad 32. Thus, the user can attach the pad 32 to the attachment portion desired by the user. However, the method for changing the attachment position of the pad 32 on the forehead contact portion 512 is not limited thereto. The attachment position of the pad 32 on the forehead contact portion 512 may be changed by a method similar to or the same as the method according to the aforementioned embodiment. In this case, the user applies rearward force to the pad 32 so as to pull the pad 32 rearward while elastically deforming the truncated cone portions 325. Thus, the user removes the engagement protrusions 322 from the through holes into which the engagement protrusions 322 were inserted. The user then inserts the engagement protrusions 322 into through holes provided in, of the attachment portions 516A to 516C, the attachment portion to which the user desires to attach the pad 32 while elastically deforming the truncated cone portions 325 of the engagement protrusions 322.

Third Modification

Figure 7:
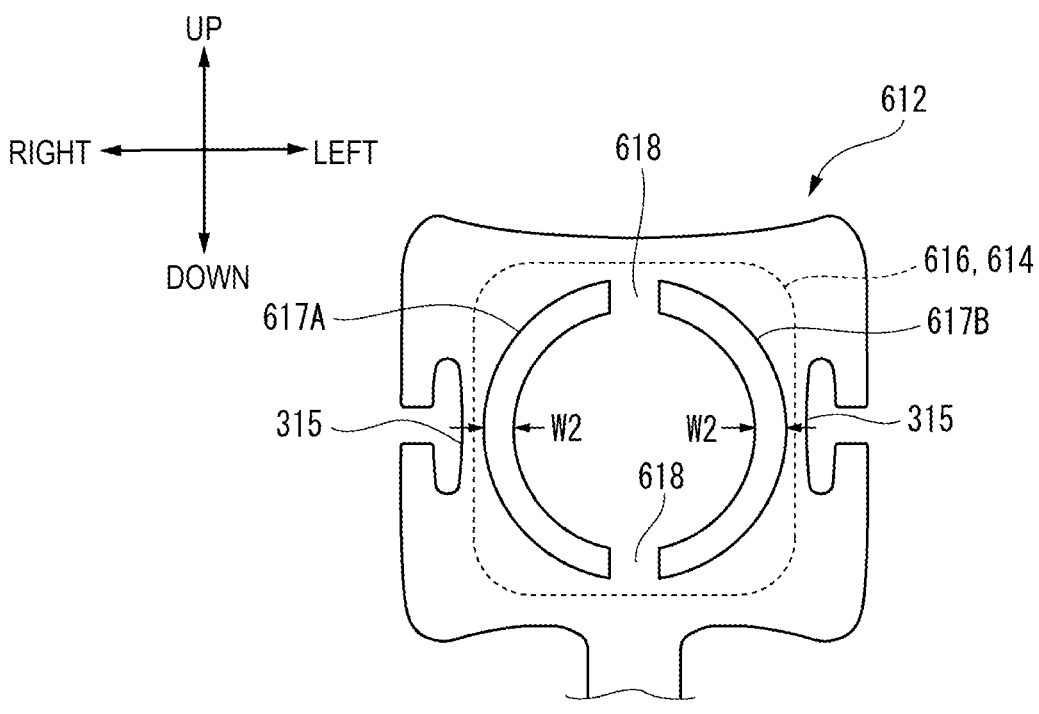
FIG. 7 is a view illustrating a forehead contact portion according to a third modification.

FIG. 7 is a view illustrating a forehead contact portion 612 according to a third modification. The forehead contact portion 612 is different from the forehead contact portion 312 at a point that an adjustment portion 614 different in configuration from the adjustment portion 314 is provided. The adjustment portion 614 may include one slide attachment portion 616 (an example of an attachment portion). The slide attachment portion 616 may include a right slide groove 617A (an example of an engagement recess) and a left slide groove 617B (an example of an engagement recess) which are shaped like semicircular arcs respectively to be combined into an approximately circumferential shape of one circle having discontinuous portions 618 provided substantially at the centers of upper and lower end portions of the forehead contact portion 612.

Widths W2 of the right slide groove 617A and the left slide groove 617B are smaller than the diameter d3 of the cylindrical column portion 324 of the pad 32. The engagement protrusions 322 of the pad 32 are engaged with the right slide groove 617A and the left side groove 617B respectively.

To change the attachment position of the pad 32 on the forehead contact portion 612 according to the third modification, the user slides (moves) the pad 32 so as to rotate the pad 32 along the circumference of the circle of the slide attachment portion 616 while elastically deforming the cylindrical column portion 324 of the pad 32. That is, the user can adjust a position and an angle (posture) of the pad 32 with respect to the forehead contact portion 612 by moving the pad 32 along the right slide groove 617A and the left slide groove 617B of the slide attachment portion 616 without detaching the pad 32 from the forehead contact portion 612.

The aforementioned embodiment and the aforementioned modifications are to make the presently disclosed subject matter easy to understand, and do not limit the presently disclosed subject matter. The presently disclosed subject matter can be changed or modified without departing from its gist.

In the aforementioned embodiment and the aforementioned modifications, the engagement recesses are provided in the forehead contact portion, and the pad is provided with two engagement protrusions. However, the presently disclosed subject matter is not limited thereto. For example, one through hole (engagement recess) may be provided at the center of the forehead contact portion, and the pad may be provided with one engagement protrusion. When, for example, the engagement protrusion is shaped like a circle in section, the pad can rotate around the through hole. Accordingly, the user can adjust the angle (posture) of the pad with respect to the forehead contact portion.

In the aforementioned embodiment and the aforementioned modifications, the position of the pad with respect to the forehead contact portion or the position and the angle (posture) of the pad with respect to the forehead contact portion is adjusted. However, only the angle (posture) of the pad with respect to the forehead contact portion may be adjusted. For example, assume that the pad is configured to move rotationally in the up/down direction in the state in which the pad has been attached to the forehead contact portion. In this case, the user can adjust the angle (posture) of the pad with respect to the forehead contact portion by moving the pad rotationally in the up/down direction. Incidentally, the number of the through holes (engagement recesses) of the forehead contact portion or the engagement protrusions of the pad, and the positions and the shapes of the through holes or the engagement protrusions are not limited as long as the angle (posture) of the pad with respect to the forehead contact portion can be adjusted.

In the aforementioned embodiment and the aforementioned modifications, the engagement protrusions and the engagement recesses are provided in the pad and the forehead contact portion respectively. However, the engagement protrusions and the engagement recesses may be provided in the forehead contact portion and the pad respectively.

In the aforementioned embodiment and the aforementioned modifications, the engagement recesses are through holes. However, the engagement recesses may be bottomed holes.

In the aforementioned embodiment and the aforementioned modifications, the mask 2 is provided with the cushion member 23. However, the mask 2 may be not provided with the cushion member 23.

In the aforementioned embodiment, the first modification, and the second modification, each of the attachment portions has two through holes paired in the left/right direction. However, the attachment portion may further have another through hole provided between the two through holes. In this case, the attachment portion includes three through holes.

In the third modification, the slide attachment portion 616 has an arc shape curved smoothly. However, the slide attachment portion 616 may have an arc shape curved zigzag.

In the aforementioned embodiment and the aforementioned modifications, each of the bands 41 is shaped like a belt. However, the band 41 is not limited to the belt shape. The band 41 can be formed into any other shape as long as the band 41 can be placed on the forehead or the head of the patient.

What is claimed is:

1. A mask outer frame unit comprising:
a mask outer frame configured to mount on a mask attached to a face of a patient; and
a pad configured to abut against the face of the patient; wherein:
the mask outer frame includes a forehead contact portion that is disposed so as to make the pad abut against a forehead of the patient;
the forehead contact portion includes an adjustment portion to which the pad is configured to attach removably and that is configured to adjust at least one of an angle of the pad with respect to the forehead contact portion and a position of the pad with respect to the forehead contact portion;
the adjustment portion includes an attachment portion configured to attach the pad thereto, the attachment portion including a pair of engagement recesses that extend in a predetermined direction along a face of the forehead contact portion, the predetermined direction configured to be a left-right direction of the face of the patient when worn by the patient;
one of the pair of engagement recesses has a first opening portion, the first opening portion being disposed to partially overlap with a first end portion, in the left right direction, of the forehead contact portion;
the other of the pair of engagement recesses has a second opening portion, the second opening portion being disposed to partially overlap with a second end portion, in the left-right direction, of the forehead contact portion opposite to the first end portion; and
the pair of engagement recesses constitutes through holes or through grooves that pass through the forehead contact portion from a side where the pad is attached to an opposite side of the forehead contact portion.

2. The mask outer frame unit according to claim 1, wherein:
the adjustment portion includes a plurality of attachment portions for attaching the pad thereto, the plurality of attachment portions including the attachment portion.

3. The mask outer frame unit according to claim 2, wherein:
each of the attachment portions includes a pair of left and right attachment regions; and
the attachment portions are disposed side by side in an up/down direction in the forehead contact portion.

4. The mask outer frame unit according to claim 1, wherein:
the pad includes an engagement protrusion for engaging the pad with one of the engagement recesses of the attachment portion.

5. The mask outer frame unit according to claim 1, wherein:
the pair of engagement recesses is the through holes.

6. The mask outer frame unit according to claim 1, wherein:
the pair of engagement recesses is formed so that diameters of the engagement recesses are larger toward the pad.

7. A mask unit comprising:
the mask outer frame unit according to claim 1; and
a mask configured to attach to the face of the patient.

8. A band-including mask unit comprising:
the mask unit according to claim 7; and
bands configured to be placed into the mask unit and configured to attach to the patient.

9. A mask outer frame configured to mount on a mask attached to a face of a patient, wherein:
the mask outer frame comprises a forehead contact portion that is disposed so as to make a pad abuttable against the face of the patient abut against a forehead of the patient;
an adjustment portion for removably attaching the pad thereto is provided in the forehead contact portion;
the adjustment portion is configured to adjust at least one of an angle of the pad with respect to the forehead contact portion and a position of the pad with respect to the forehead contact portion;
the adjustment portion includes an attachment portion configured to attach the pad thereto, the attachment portion including a pair of engagement recesses that extend in a predetermined direction along a face of the forehead contact portion, the predetermined direction configured to be a left-right direction of the face of the patient when worn by the patient;
one of the pair of engagement recesses has a first opening portion, the first opening portion being disposed to partially overlap with a first end portion, in the left-right direction, of the forehead contact portion;
the other of the pair of engagement recesses has a second opening portion, the second opening portion being disposed to partially overlap with a second end portion of the forehead contact portion, in the left-right direction, opposite to the first end portion; and
the pair of engagement recesses constitutes through holes or through grooves that pass through the forehead contact portion from a side where the pad is attached to an opposite side of the forehead contact portion.

\* \* \* \* \*